United States Patent
Weir

(10) Patent No.: US 6,300,275 B1
(45) Date of Patent: Oct. 9, 2001

(54) RESILIENT SUPERABSORBENT COMPOSITIONS

(75) Inventor: Joseph L. Weir, Midland, MI (US)

(73) Assignee: The Dow Chemical Company, Midland, MI (US)

(*) Notice: Subject to any disclaimer, the term of this patent is extended or adjusted under 35 U.S.C. 154(b) by 0 days.

(21) Appl. No.: 09/403,363

(22) PCT Filed: Apr. 28, 1998

(86) PCT No.: PCT/US98/08505

§ 371 Date: Oct. 20, 1999

§ 102(e) Date: Oct. 20, 1999

(87) PCT Pub. No.: WO98/48857

PCT Pub. Date: Nov. 5, 1998

Related U.S. Application Data

(60) Provisional application No. 60/044,363, filed on Apr. 29, 1997.

(51) Int. Cl.[7] ........................................ B01J 20/26
(52) U.S. Cl. ............................................... 502/402
(58) Field of Search ............................. 502/402; 604/368, 604/372; 428/96, 304.4

(56) References Cited

U.S. PATENT DOCUMENTS

| Re. 33,839 | 3/1992 | Chmelir et al. ...................... 604/368 |
| 5,115,011 | 5/1992 | Harada et al. ....................... 524/419 |
| 5,558,745 | 9/1996 | Conway et al. ....................... 162/60 |
| 5,721,295 | 2/1998 | Brüggemann et al. ................ 524/44 |

FOREIGN PATENT DOCUMENTS 41 33 699 A1    4/1993    (DE) .

OTHER PUBLICATIONS

Derwent 87–149264, Prpn. of Paper from Pulp–involves using potash alum and/or aluminum sulphate to increase absorbency while maintaining wet strength, Oct. 7, 1986.

Primary Examiner—Stuart L. Hendrickson

(57) ABSTRACT

Superabsorbent polymers having improved gel bed resiliency are prepared by dry blending the polymer with a multivalent metal salt to form a mixture; and contacting the mixture with from about 0.1 to 10 percent of binder, based on the weight of the mixture.

8 Claims, No Drawings

RESILIENT SUPERABSORBENT COMPOSITIONS

This application is related to No. 60/044,363 filed Apr. 29, 1997, and is a national storage application of PCT/US928/08505 filed Apr. 28, 1998.

This invention relates to superabsorbent compositions which contain multivalent metal salts and a process for preparing said compositions.

Superabsorbent polymers are well-known materials which commonly are used in personal care articles such as diapers. These polymers are known to absorb several times their weight of, for example, water, saline solution, urine, blood, and serous bodily fluids. However, these polymers suffer from a phenomenon called gel blocking. Gel blocking refers to decreased rate of absorbency which results from rapid swelling of particle surfaces followed by clumping of polymer gel particles. This clumping tends to shield or block part of the absorbent polymer from the fluid to be absorbed, resulting in decreased absorption per unit weight of polymer.

Because superabsorbent polymers are subject to gel blocking, it is common practice in the manufacture of diapers to mix the superabsorbent polymer with a fibrous material such as cellulose fluff used in diapers. One purpose of the fluff is to separate the particles of superabsorbent polymer from one another in order to decrease the degree of gel blocking. Unfortunately, fluff prices recently have risen making it uneconomical to use as much fluff as was commonly used in the past. As a result, diaper manufacturers would like to replace some of the fluff with additional superabsorbent polymer. However, replacing fluff with superabsorbent is not an ideal solution since known superabsorbents tend to gel block more in diapers having less fluff. Therefore, it would be desirable to have a superabsorbent polymer having reduced gel blocking characteristics.

U.S. Pat. No. 5,115,011 addresses the gel blocking problem by contacting a water absorbent polymer with an aqueous solution of two water soluble salts, the first being a halogen, sulfate, acetate or nitrate of aluminum, calcium or magnesium, and the second being a monovalent metal salt or ammonium salt of at least one kind of an oxyacid selected from sulfurous acid and thiosulfuric acid. A dry blend of 0.6 g aluminum sulfate and 30 g polymer is prepared in Example for Comparison 3 of the patent, and is shown to have a blocking of 70 percent or more after 5 minutes.

U.S. Pat. No. 5,578,318 discloses the preparation of superabsorbent "hydrophobic coated particles" by dry blending materials, such as non-crosslinked polyacrylate salts, with a source of multivalent ions and, optionally, then adding an alcohol, certain wetting agents, and polysiloxane derivatives. The wetted material is dried prior to use. Example XXIII of this patent discloses a blend of 2.61 weight percent AQUALON A-250, 0.21 weight percent aluminum acetate, and 97.18 weight percent water. After drying, the resulting material of this example exhibited relatively poor performance as a superabsorbent.

U.S. Pat. No. 4,090,013 discloses materials prepared from a water-soluble anionic polyelectrolyte and a polyvalent metal cation source. However, the products are s characterized in U.S. Pat. No. 5,578,318 as exhibiting gel blocking.

U.S. Pat. No. 4,693,713 discloses an absorbent for blood and serous bodily fluids, the absorbent comprising a physical mixture of certain polymers and certain compounds. The compounds are described as water soluble, present in the form of a pourable powder at ambient temperature, and not harmful to health. The patent teaches that the compound may be added to the polymer by dissolving it in the monomer solution, or that the compound can be added to the polymer preparation process at any time in dry or dissolved form. Dry blends of polymer and compound are prepared in the examples of the patent.

J0172457-A discloses a composition prepared by dry blending a superabsorbent resin and polyaluminum chloride. This publication teaches that water absorption performance is greatly decreased when a salt other than polyaluminum chloride is used.

It would be desirable to have a superabsorbent polymer with improved resistance to gel blocking and which would not require the use of oxyacids in its preparation. It would be further desirable to have a superabsorbent polymer with improved absorption, absorption under load and decreased gel blocking. Furthermore, it would be desirable to have a simpler and more efficient process to prepare materials with such properties.

The superabsorbent polymer of the invention exhibits improved gel bed resiliency. Specifically, the superabsorbent polymer composition of the invention exhibits a gel bed resiliency of at least 5 millimeters. Gel bed resiliency is a property which describes the ability of a superabsorbent polymer gel mass to rebound following compression. While not wishing to be bound by any theory, it is believed that this improved resiliency reduces gel blocking by maintaining the porosity of the gel bed. It is further believed that improved gel bed resiliency makes the superabsorbent polymer of the invention especially suitable for use in absorbent articles, such as diapers, which have high loadings of superabsorbent polymer.

The invention includes a process for preparing the improved superabsorbent polymer. The invention also includes a process for preparing an improved superabsorbent polymer, the process comprising mixing the polymer with a multivalent metal salt, then intimately contacting the mixture from 0.1 to 10 percent binder, based on the weight of the polymer and multivalent metal salt mixture, with the proviso that the contacting is conducted in the substantial absence of volatile alcohols. The invention further includes absorbent articles comprising the composition of the invention.

The improved superabsorbent polymer of the invention is prepared by mixing, preferably by dry blending, a superabsorbent polymer with a multivalent metal salt and then contacting the mixture with a binder.

In the present invention, a multivalent metal salt suitably is employed in an amount sufficient to improve the gel bed resiliency property of the superabsorbent polymer. Preferably, at least 0.5 percent of multivalent metal salt, based the weight of the mixture, is employed. More preferably, at least about 1 percent of multivalent metal salt, and most preferably at least about 2 percent of multivalent metal salt are employed. Preferably, no more than about 10 percent of multivalent metal salt are employed based on the weight of the mixture of multivalent metal salt and polymer. More preferably, no more than about 8 weight percent multivalent metal salt is employed, and most preferably, no more than 6 weight percent multivalent metal salt is employed. Preferably, the amount of multivalent metal salt employed is from 0.5 to 10 weight percent based on the weight of multivalent metal salt and polymer. More preferably, from 1 to 8 percent of multivalent metal salt are employed, and most preferably from 2 to 6 weight percent are employed.

The multivalent metal salt is preferably water soluble. Examples of preferred metal cations include the cations of Al, Fe, Zr, Mg and Zn. Preferably, the metal cation has a valence of at least +3, with Al being most preferred. Examples of preferred anions in the multivalent metal salt include halides, chlorohydrates, sulfates, nitrates and acetates, with chlorides, sulfates, chlorohydrates and acetates being preferred, chlorohydrates and sulfates being more preferred, and sulfates being most preferred. Inorganic salts are more preferred. Aluminum sulfate is the most preferred multivalent metal salt and is readily commercially available. The preferred form of aluminum sulfate is hydrated aluminum sulfate, more preferably aluminum sulfate having from 12 to 14 waters of hydration. Mixtures of multivalent metal salts can be employed. Preferably, the contacting of the polymer and multivalent metal salt is conducted in the substantial absence of a monovalent metal salt or ammonium salt of at least one kind of an oxyacid selected from sulfurous acid and thiosulfuric acid. In a preferred embodiment, the contacting is conducted in the substantial absence of divalent metal salts.

The polymer and multivalent metal salt suitably are mixed, preferably dry blended, using means well known to those skilled in the art. Examples of suitable blending equipment include, for example, jar tumblers, plowshare mixers, paddle blenders, ribbon blenders, rotary blenders and high speed rotary blenders. Preferably the polymer and multivalent metal salt are dry blended in a manner such that a substantially uniform mixture of the two materials is obtained.

Following the preparation of the mixture of multivalent metal salt and polymer, the mixture is contacted with a binder. In a preferred embodiment, of the invention, the binder is sprayed onto the mixture of multivalent metal salt and polymer while it is still in the mixing or dry blending equipment. Preferably the contacting is conducted in such a manner that the binder is substantially uniformly distributed throughout the mixture. The pressure and temperature of the contacting step are not critical.

The binder suitably is employed in an amount which is sufficient to ensure that a substantially uniform mixture of the salt and the superabsorbent polymer is maintained. Preferably, at least 0.1 percent of binder, based on the weight of the mixture, is employed. More preferably, at least about 0.5 percent of binder, and most preferably at least about 1 percent of binder is employed. Preferably, no more than about 10 percent of binder is employed based on the weight of the mixture of multivalent metal salt and polymer. More preferably, no more than about 5 weight percent binder is employed, and most preferably, no more than 3 weight percent binder are employed.

The binder preferably is a liquid at ambient temperature. The binder is water or a nonvolatile organic compound, that is, an organic compound having a boiling point of at least 150° C. Examples of preferred binders include, for example: water; light oils, such as mineral oil; and polyols, that is, hydrocarbons having at least 2 hydroxyl moieties, such as propylene glycol, glycerin, poly(ethylene glycol), and VORANOL 230-238. VORANOL 230-238 brand polyol (available from The Dow Chemical Company) is a preferred binder, and water is a more preferred binder. Mixtures of binders can be employed. Optionally, the binder may include a multivalent metal salt identified hereinabove. In such a case, the total amount of multivalent metal salt in the composition of the invention is as described hereinabove.

Following the binder contacting step, the composition of the invention is recovered from the mixing equipment and is ready for use. The composition optionally may be dried.

The water-swellable or lightly crosslinked hydrophilic polymers suitably employable in the present invention can be any of the known hydrophilic polymers which are capable of absorbing large quantities of fluids. In particular, water-absorbent polymers useful in this invention are water-absorbent polymers which contain carboxyl moieties. Preferably, at least about 0.01 equivalent of carboxyl groups are present per 100 grams of the water-absorbent resin.

Among preferred carboxyl-containing water absorbent polymers are hydrolyzates of starch-acrylonitrile graft copolymers, partially neutralized products of starch-acrylic acid or starch-polyvinyl alcohol graft copolymers, saponification products of vinyl acetate acrylic ester copolymers, derivatives of copolymers of isobutylene and maleic anhydride, hydrolyzates of acrylonitrile copolymers, crosslinked products of hydrolyzates of acrylonitrile copolymers, crosslinked carboxymethyl cellulose, polyaspartate hydrolyzates of acrylamide copolymers, crosslinked products of hydrolyzates of acrylamide copolymers, partially neutralized products of polyacrylic acids and crosslinked products of partially neutralized polyacrylic acids.

Examples of some suitable polymers and processes, including gel polymerization processes, for preparing them are disclosed in U.S. Pat. Nos. 3,997,484; 3,926,891; 3,935,099; 4,090,013; 4,093,776; 4,340,706; 4,446,261; 4,683,274; 4,459,396; 4,708,997; 4,076,663; 4,190,562; 4,286,082; 4,857,610; 4,985,518; and 5,145,906, which are incorporated herein by reference. In addition, see Buchholz, F. L. and Graham, A. T., "Modern Superabsorbent Polymer Technology," John Wiley & Sons (1998). Such hydrophilic polymers are prepared from water-soluble α,β-ethylenically unsaturated monomers such as monocarboxylic acids, polycarboxylic acids, acrylamide and their derivatives.

Suitable α,β-ethylenically unsaturated monomers include, for example, acrylic acid, methacrylic acid, crotonic acid, isocrotonic acid and alkali metal salts and ammonium salts thereof; itaconic acid, acrylamide, methacrylamide and 2-acrylamido-2-methyl-1-propane sulfonic acid and its salts. The preferred monomers include acrylic acid and methacrylic acid and their respective salt forms such as alkali metal or ammonium salts.

The water-soluble monomers useful in the present invention may be used in amounts ranging from 10 percent to 80 percent by weight based on the total weight of the aqueous monomer solution. Preferably, the amount ranges from 15 percent to 60 percent based on the total weight of the aqueous monomer solution.

Optionally, minor amounts of other water-soluble, unsaturated monomers, such as alkyl esters of the acid monomers, for example, methyl acrylate or methyl methacrylate may be present in the water absorbent polymer. In addition, certain grafting polymers, such as, for example, polyvinyl alcohol, starch and water soluble or swellable cellulose ethers may be employed to prepare products having superior properties. Such grafting polymers, when employed, are used in amounts up to about 10 weight percent based on the α,β-ethylenically unsaturated monomer. Further, it may be advantageous to include a chelating agent to remove trace metals from solution, for example, when a metal reaction vessel is employed. One such chelating agent is VERSENEX™ V-80 (an aqueous solution of the pentasodium salt of diethylenetriamine pentacetic acid) (Trademark of The Dow Chemical Company). Such chelating agents, when employed, are generally used in amounts between 100 and 2000 ppm based on the α,β-ethylenically unsaturated monomer.

It is desirable to obtain a level of conversion of monomer to polymer of at least about 95 percent. The polymerization may be carried out using acid monomers that are not neutralized or that have been neutralized or partially neutralized prior to the polymerization. Neutralization is conveniently achieved by contacting the aqueous monomer with an amount of basic material sufficient to neutralize between 20 and 95 percent of the acid groups present in the acid monomers. Preferably, the amount of basic material will be sufficient to neutralize between about 40 percent and 85 percent, and most preferably between about 55 percent and about 75 percent of the acid groups present in the acid monomers. When pre-neutralizing the monomer solution, it is important to control the neutralization conditions so that the heat of neutralization does not cause the premature polymerization of the monomer mixture.

Compounds which are useful to neutralize the acid groups of the monomer are typically those which will sufficiently neutralize the acid groups without having a detrimental effect on the polymerization process. Such compounds include alkali metal hydroxides, and alkali metal carbonates and bicarbonates. Preferably, the material used to neutralize the monomer is sodium or potassium hydroxides or carbonates. In determining the desired degree of neutralization, care must be taken to ensure that the pH of the resulting crosslinked absorbent polymer, which will be contacted with or dispersed in an aqueous fluid to be absorbed, is maintained in a range appropriate for the applications for which the polymer is intended. Alternatively, the polymerization may be carried out employing unneutralized monomers and thereafter neutralizing, as is known in the art.

Conveniently, a conventional vinyl addition polymerization initiator is used in the polymerization of the water-soluble monomers and the crosslinking agent. A free radical polymerization initiator which is sufficiently soluble in the monomer solution to initiate polymerization is preferred. For example, water soluble persulfates such as potassium persulfate, ammonium persulfate, sodium persulfate, and other alkali-metal persulfates, hydrogen peroxide and water soluble azo-compounds such as 2,2'-azobis (2-amidinopropane HCl) may be used. Some of these initiators, such as hydrogen peroxide, can be combined with reducing substances such as sulfites or amines to form known redox type initiators. The total amount of initiators used may range from 0.01 to 1.0 weight percent, preferably 0.01 to 0.5 weight percent, based on the total weight of $\alpha,\beta$-ethylenically unsaturated monomer reactants.

The water-absorbent resin will preferably be lightly crosslinked to render it water-insoluble and water-swellable. The desired crosslinked structure may be obtained by the copolymerization of the selected water-soluble monomer and a crosslinking agent possessing at least two polymerizable double bonds in the molecular unit. The crosslinking agent is present in an amount effective to crosslink the water-soluble polymer. The preferred amount of crosslinking agent is determined by the desired degree of absorption capacity and the desired strength to retain the absorbed fluid, that is, the desired absorption under load (AUL). Typically, the crosslinking agent Is used in amounts ranging from 0.0005 to 5 parts by weight per 100 parts by weight of $\alpha,\beta$-ethylenically unsaturated monomer used. More preferably, the amount ranges from 0.1 to 1 part by weight per 100 parts by weight of the $\alpha,\beta$-ethylenically unsaturated monomer. Usually, if an amount over about 5 parts by weight of crosslinking agent per 100 parts monomer is used, the resulting polymer has too high a crosslinking density and exhibits a reduced absorption capacity and increased strength to retain the absorbed fluid. If the crosslinking agent is used in an amount less than about 0.0005 part by weight per 100 parts monomer, the polymer usually has too low a crosslinking density, and when contacted with the fluid to be absorbed becomes sticky and exhibits a lower initial absorption rate.

While the crosslinking agent will typically be soluble in the aqueous solution of the $\alpha,\beta$-ethylenically unsaturated monomer, the crosslinking agent may be merely dispersible in such a solution, without negative implications. The use of such dispersing agents is disclosed in U.S. Pat. No. 4,833,222, incorporated herein by reference. Suitable dispersing agents include carboxymethyl cellulose suspending aids, methyl cellulose, hydroxypropyl cellulose, and polyvinyl alcohol. Such dispersing agents are typically provided at a concentration between about 0.005 and about 0.1 weight percent, based on the total weight of $\alpha,\beta$-ethylenically unsaturated monomer reactants.

Typical crosslinking agents include monomers having in one molecule 2 to 4 groups selected from the group consisting of $CH_2=CHCO-$, $CH_2=C(CH_3)CO-$ and $CH_2=CH-CH_2-$. Exemplary crosslinking agents are diacrylates and dimethacrylates of ethylene glycol. diethylene glycol, triethylene glycol, propylene glycol, 1,4-butanediol, 1,5-pentanediol, 1,6-hexanediol, neopentyl glycol, trimethylolpropane and pentaerythritol; triacrylates and trimethacrylates of trimethylolpropane and pentaerythritol; highly ethoxylated trimethylol propane triacrylate; tetracrylate and tetramethacrylate of pentaerythritol; and tetraallyloxyethane.

As noted in WO 93/05080, published on Mar. 18, 1993, incorporated herein by reference, a certain class of crosslinking agents yields particularly preferred absorptive properties. Such preferred crosslinking agents include methylenebisacrylamide, bis(acrylamido)acetic acid and its salts, allyl acrylate, allyl methacrylate, and esters or amides having both a vinyl and an allyl functionality. Other particularly preferred crosslinking agents and methods include those disclosed in WO 94/20547, published on Sep. 15, 1994, incorporated herein by reference. Such preferred crosslinking agents include mixtures of polyvinyl compounds such as, for example, highly ethoxylated trimethylolpropane triacrylate and allyl methacrylate, and polyglycols such as, for example, polyethylene glycol.

In a preferred embodiment for making polymers useful in the practice of this invention, an aqueous solution of the $\alpha,\beta$-ethylenically unsaturated monomer in the partially neutralized form, the crosslinking agent, the initiator and a grafting polymer substrate, if desired, is prepared. The polymerization of the mixture may be initiated by elevating the temperature of the mixture containing the initiator or by using a redox-type initiator as described above. Generally, the temperature at which polymerization will begin ranges from 10° C. to 45° C. The temperature at which the polymerization is carried out is highly dependent on the type of monomers used and the specific initiator system employed. Preferably, the maximum temperature of polymerization ranges from 50° C. to 100° C., most preferably from 60° C. to 100° C. The method by which the temperature of the polymerization is controlled is not critical so long as sufficient cooling is present to remove the heat which is generated during the polymerization.

The resultant polymer is typically pre-sized and dried using means well-known in the art. Suitable drying means include fluidized bed driers, rotary driers, forced air ovens and through-circulation band dryers,. In some instances, drying will occur in two or more stages, that is multi-stage drying. In multi-stage drying, the pre-sized polymer particles are partially dried in the initial stage or stages, for example, the pre-sized polymer particles are dried to less than about 25, preferably less than about 20 percent moisture level. Drying to less than about 10, preferably less than about 5 percent moisture level is accomplished during the completion of drying stages. During the initial stage or stages of drying, the pre-sized particles typically fuse together into sheets. Following the completion of drying, the polymer is more completely sized to form particles having an average diameter less than about 0.8 mm. During such sizing, dust, characterized by extremely small particle sizes may result, that is, particle sizes less than or equal to 10 microns. The amount of dust generated will vary based on manufacturing procedures. Preferably, the final polymer product has an average particle size of at least 160 mm.

To improve absorptive properties, the dried particles may be heat treated in accordance with the procedures set forth in WO 93/05080, and/or WO 94/20547, incorporated herein by reference. In particular, the dried particles are heated for a time sufficient to increase the modulus, and/or the absorbency under load (AUL). An oxidizing agent, such as a bromate, chlorate, chlorite, or mixture thereof, may be uniformly distributed within the water absorbent polymer prior to such heat treatment to enhance one or more of the preceding properties. Such heat treatment is preferably carried out at a temperature of at least about 170° C., more preferably of at least 180° C., and most preferably of at least about 190° C. Such heat treatment is preferably carried out at a temperature of less than about 250° C., more preferably less than about 240° C. Advantageously, however, the composition of the present invention has excellent AUL and modulus without requiring heat treatment.

The time period for heat treatment should be sufficient to effect an improvement in absorptive properties. The exact times of heat treatment required will be affected by the equipment chosen, and can be determined empirically by examination of product properties. Preferably, the time is at least about 3 minutes, and more preferably at least about 5 minutes. If the time is too long, the process becomes uneconomical and a risk is run that the absorbent resin may be damaged. Preferably, the maximum time of heating is about 150 minutes or less, more preferably 60 minutes or less.

The method of heat treatment is not critical. For example, forced air ovens, fluidized bed heaters, heated screw conveyors, and the like may be successfully employed. If desired, the heated polymer may be remoisturized for ease in handling. While such remoisturization may serve to decrease the amount of unassociated dust, it may lead to clumping of the polymer product.

Another way to improve absorptive properties of the polymer particles may be to surface crosslink the polymer particles. Procedures for surface crosslinking are well known in the art and described in, for example, DE 4244548, DE 4020780, EP 605150, U.S. Pat. Nos. 4,734,478, and 4,666,983. These procedures, may increase the modulus and/or the absorbency under load of the polymer particles.

Advantageously, the process of the invention does not require dispersing agents, such as volatile alcohols or wetting agents. Preferably, the process of the invention is conducted in the substantial absence of volatile alcohols, and more preferably is conducted in the absence of volatile alcohols. For the purposes of the present invention, volatile alcohols are alcohols having a boiling point of less than 150° C.

The composition of the invention can optionally include other additives such as, for example, anticaking agents. Anticaking agents are well-known. Silica is an example of a preferred anticaking agent.

The composition of the invention exhibits improved gel bed resiliency. Preferably, the composition has a gel bed resiliency of at least about 5 mm, more preferably at least about 7 mm, even more preferably at least about 9 mm, and most preferably at least about 11 mm.

In addition to having excellent gel bed resiliency and reduced gel blocking characteristics, the composition of the invention exhibits more uniform centrifuge capacity than dry blended compositions prepared in the absence of a binder, and exhibits improved attrition resistance. The compositions of the invention preferably are free flowing and nonagglomerated. Surprisingly, the compositions of the invention have improved permeability.

The superabsorbent polymers of this invention are useful in the manufacture of moisture absorbent articles, such as disposable diapers, sanitary napkins, incontinence garments and bandages. The superabsorbent compositions of this invention are particularly useful in the manufacture of thin and ultra thin disposable diapers which have excellent moisture absorbance capacity, fluid distribution properties and reduced leakage.

For the purposes of the present invention, the term "fluff" is given its meaning as understood by those of ordinary skill in the art.

In making absorbent articles with the compositions of this invention, the superabsorbent composition may be mixed with, attached to, layered in, or dispersed in a porous matrix of fibers. Such matrices are made with hydrophilic fibers such as wood pulp or fluff, cotton linters, and synthetic fibers or a mixture of the fibers and the wood fluff. The fibers can be loose or joined as in nonwovens. The synthetic fibers can be polyethylene, polypropylene, polyesters, copolymers of polyesters and polyamides. The synthetic fibers may be meltblown fibers or fibers which have been treated to render them hydrophilic. Additionally, the superabsorbent polymers of the invention may be incorporated in the absorbent article in a compartment or localized area of the absorbent structure.

Absorbent articles, such as disposable diapers, typically are made with a liquid-impermeable backing material, a liquid-permeable bodyside facing material and the liquid-absorbing composite sandwiched between the backing material and the facing material. The liquid-impermeable backing material can be made from commercially available polyolefin film and the liquid-permeable facing material can be made from a commercially available nonwoven material, such as spunbonded or corded fibrous web which is wettable and capable of passing urine.

The absorbent articles of the invention may comprise from 5 percent to 95 percent by weight of the superabsorbent polymers of the invention. In a typical absorbent article, the superabsorbent polymer of the invention may be dispersed in a fiber matrix in which the superabsorbent is present in an amount from about 30 to 70 weight percent and the fiber matrix comprising 70 to 30 weight percent of the article. In another form of absorbent article, the superabsorbent may be present in a containment structure in which the superabsorbent polymer is present in an amount of about 30 to 95 percent by weight. Combinations of dispersed superabsorbent polymer arid contained superabsorbent polymer are also known.

The improved gel bed resiliency of the superabsorbent polymer composition of the invention makes the composition especially useful in absorbent articles which have high loadings of superabsorbent polymer. This can be expressed as the polymer to fluff ratio. Preferred absorbent articles of the invention have a weight ratio of superabsorbent polymer and aluminum sulfate to fluff of at least 0.3, more preferably at least 0.5 and most preferably at least 1. Construction of diapers and other absorbent articles is well known, and materials useful as fluff in absorbent articles are also well known. See, for example. U.S. Pat. No. 4,795,454.

The superabsorbent polymers of this invention can be used in the manufacture of absorbent articles such as those described in U.S. Pat. Nos. 3,669,103; 3,670,731; 4,654,039; 4,699,823; 4,430,086; 4,973,325; 4,892,598; 4,798,603; 4,500,315; 4,596,567; 4,676,784; 4,938,756; 4,537,590; 4,935,022; 4,673,402; 5,061,259; 5,147,343; 5,149,335; and 5,156,902; the teachings of which are hereby incorporated by reference.

Specific Embodiments of the Invention

The following examples are given to illustrate the invention and should not be construed as limiting. All parts and percentages are by weight unless otherwise indicated.

EXAMPLE 1

1300 g of DRYTECH 535 brand superabsorbent polymer and 26 g of powdered $Al_2(SO_4)_3$ 14 $H_2O$ were loaded into a laboratory blender. The blender was started and the powders were blended until well mixed. Next, 27 g of a 3.3 percent solution of VORANOL 230–238 in water was sprayed onto the powders as a fine mist while continuing to blend the powders. Following addition of the solution, blending was continued until the mixture becomes free flowing. Results of physical property testing on the final mixture were summarized in Table 1.

EXAMPLE 2

The procedure of Example 1 was repeated except that 52 g of powdered $Al_2(SO_4)_3$ 14 $H_2O$ was employed.

EXAMPLE 3

The procedure of Example 1 was repeated except that 78 g of powdered $Al_2(SO_4)_3$ 14 $H_2O$ and 40.5 g of VORANOL solution were employed.

EXAMPLE 4

The procedure of Example 2 was repeated except that the powdered $Al_2(SO_4)_3$ 14 $H_2O$ was replaced with aluminum chlorohydrate powder, and 27.9 g of a 3.2 percent VORANOL solution were employed.

EXAMPLE 5

The procedure of Example 4 was repeated except that 26 g of powdered $Al_2(SO_4)_3$ 14 $H_2O$ and 26 g of aluminum chlorohydrate powder were employed.

EXAMPLE 6

1300 g of DRYTECH 2035 brand superabsorbent polymer and 53 g of powdered $Al_2(SO_4)_3$ 14 $H_2O$ were loaded into a laboratory blender. The blender was started and the powders were blended until well mixed. Next, 27.9 g of a 3.2 percent solution of VORANOL 230–238 in water was sprayed onto the powders as a fine mist while continuing to blend the powders. Following addition of the solution, blending was continued until the mixture became free flowing.

EXAMPLE 7

1200 g of DRYTECH 535 brand superabsorbent polymer and 32 g of powdered $Al_2(SO_4)_3$ 14 $H_2O$ was loaded to a laboratory blender. The blender was started and the powders were blended until well mixed. Next, 40 g of a 4 percent solution of $Al_2(SO_4)_3$ 14 $H_2O$ in water was sprayed onto the powders as a fine mist while continuing to blend the powders. Following addition of the solution, blending was continued until the mixture became free flowing.

EXAMPLE 8

1200 g of DRYTECH 535 brand superabsorbent polymer and 24 g of powdered $Al_2(SO_4)_3$ 14 $H_2O$ was loaded to a laboratory blender. The blender was started and the powders were blended until well mixed. Next, 48 g of a 50 percent solution of aluminum chlorohydrate in water was sprayed onto the powders as a fine mist while continuing to blend the powders. Following addition of the solution, blending was continued until the mixture became free flowing.

TABLE 1

| Example | Centrifuge Capacity (g/g) | PSI AUL (g/g) | 0.6 PSI AUL (g/g) | GBR value (mm) |
|---|---|---|---|---|
| DRYTECH 535 control | 30.1 | 25 | 10.8 | 0.5 |
| DRYTECH 2035 control | 29.5 | 32 | 26 | 4.5 |
| Example 1 | 27.5 | 27 | 15 | 8.0 |
| Example 2 | 27.1 | 27 | 18 | 10.0 |
| Example 3 | 26.7 | 27 | 19 | 12.0 |
| Example 4 | 28.7 | 25 | 12 | 10.0 |
| Example 5 | 27.9 | 27 | 16 | 9.0 |
| Example 6 | 27.7 | 28 | 23 | 13.5 |
| Example 7 | 27.4 | 27 | 20 | 9.5 |
| Example 8 | 27.1 | 28 | 19 | 9.0 |

Gel Bed Resilience (GBR) Test

First, 10 g of 0.9 percent aqueous saline solution was measured into a 400-ml beaker. Next, 10 g of superabsorbent polymer was poured into the saline solution and the mixture was stirred until gelled. The resulting gel was then allowed to equilibrate by standing for 15 minutes. Next, 5 g of the swollen gel was weighed into a 2.54 cm (1)" inside diameter cylinder. A plastic piston weighing 3.6 g and a 200 g weight were then placed in the cylinder and were allowed to compress the gel. The height of the compressed gel within the cell was measured and recorded in mm as $H_c$. The weight was then removed and the height of the decompressed gel was measured and recorded in mm as $H_d$.

The GBR value is calculated using the following formula.

$$GBR = H_c + H_d - 2(H_o)$$

Where: $H_c$=height in mm of compressed gel.

$H_d$=height in mm of gel after decompression.

$H_o$=theoretical height in mm of 5 g of a gel with zero void volume.

Centrifuge Capacity Method

A 0.200 g sample of polymer, 300–600 mm (30–50 mesh) cut, was added to a 6.4×7.6 cm (2.5×3 inch) rectangular bag, and the bag was sealed. The sealed bags, including blanks were held in a 0.9 percent NaCl solution for 30 minutes. The wet bags were then placed in the basket of a centrifuge (Clay Adams Dynac II, Model #0103) and centrifuged at 1600 rpm for 3 minutes. The bags were removed and weighed and the swelling capacity was calculated.

Absorbency Under Load

Absorbency under load (AUL) was determined as follows. A polymer sample of average diameter between 300–600 mm (30–50 mesh) cut, weighing 0.160±0.005 g, was placed into a cylindrical cell. The desired load was applied (2.0 or 3.9 kPa loads respectively for 0.3 or 0.6 psi load) and the polymer was allowed to imbibe 0.9 weight percent NaCl through a screen underneath the polymer, at zero liquid pressure head relative to the bottom of the gel layer. The mass loss of the reservoir or the mass gain of the sample group was recorded to determine the swelling as a function of applied pressure. The swelling capacity under the applied load was reported as the mass of liquid gained per mass of polymer.

What is claimed is:

1. A process, the process comprising dry blending a polymer with at least 0.5 percent of a multivalent metal salt, based on the weight of the mixture of the polymer and the salt, then intimately contacting the mixture with from 0.1 to 10 percent binder, based on the weight of the polymer and multivalent metal salt mixture, said binder being selected from the group consisting of water and an organic compound having a boiling point of at least 150° C., wherein the contacting is conducted in the substantial absence of a volatile alcohol and in the substantial absence of a monovalent metal salt or ammonium salt of an oxyacid selected from sulfurous acid and thiosulfuric acid; and wherein the polymer is a polymer selected from saponification products of vinyl acetate acrylic ester copolymers, derivatives of copolymers of isobutylene and maleic anhydride, hydrolyzates of acrylonitrile copolymers, cross-linked products of hydrolyzates of acrylonitrile copolymers, polyaspartate hydrolyzates of acrylamide copolymers, cross-linked products of hydrolyzates of acrylamide copolymers, partially neutralized products of polyacrylic acids and cross-linked products of partially neutralized acids.

2. The process of claim 1 wherein the amount of multivalent metal salt is from 1 to 8 percent and the gel bed resiliency property of the superabsorbent is at least 7 mm.

3. The process of claim 1 wherein the multivalent metal salt is aluminum sulfate or aluminum chlorohydrate or a mixture thereof.

4. The process of claim 1 wherein the binder is water.

5. The process of claim 1 wherein the amount of multivalent metal salt is from 0.5 to 10 weight percent.

6. The process of claim 5 wherein the amount of multivalent metal salt is from 1 to 8 percent.

7. The process of claim 6 wherein the amount of multivalent metal salt is from 2 to 6 percent.

8. A process comprising:

A) dry blending a water-insoluble superabsorbent polymer with from 0.5 to 8 percent of aluminum sulfate, based on the weight of the polymer, to form a mixture; and B) contacting the mixture with from about 0.5 to 10 percent of water, based on the weight of the mixture, with the proviso that the contacting is conducted in the substantial absence of a volatile alcohol and in the substantial absence of a monovalent metal salt or ammonium salt of an oxyacid selected from sulfurous acid and thiosulfuric acid.

* * * * *